United States Patent [19]

Vander Heyden

[11] Patent Number: 5,357,809
[45] Date of Patent: Oct. 25, 1994

[54] VOLUMETRIC FLOW CORRECTOR HAVING A DENSITOMETER

[75] Inventor: William H. Vander Heyden, Mequon, Wis.

[73] Assignee: Badger Meter, Inc., Milwaukee, Wis.

[21] Appl. No.: 48,349

[22] Filed: Apr. 14, 1993

[51] Int. Cl.[5] ............................................. G01F 15/04
[52] U.S. Cl. ..................................... 73/861.02; 374/36
[58] Field of Search ....................... 73/3, 861.02, 861; 374/36, 37

[56] References Cited

U.S. PATENT DOCUMENTS

| | | | |
|---|---|---|---|
| 3,777,562 | 12/1973 | Clingman | 73/309 |
| 4,062,236 | 12/1977 | Clingman | 73/190 |
| 4,125,018 | 11/1978 | Clingman | 73/190 |
| 4,125,123 | 11/1978 | Clingman | 73/190 |
| 4,285,245 | 8/1981 | Kennedy | 73/861 |
| 4,351,614 | 9/1982 | Garnier | 374/37 |
| 4,380,400 | 4/1983 | Searle | 374/37 |
| 4,396,299 | 8/1983 | Clingman et al. | 374/37 |
| 4,419,898 | 12/1983 | Zanker et al. | 73/3 |
| 4,446,748 | 5/1984 | Clingman et al. | 73/863 |
| 4,527,435 | 7/1985 | Hall et al. | 73/863 |
| 4,562,744 | 1/1986 | Hall et al. | 73/861 |
| 4,614,721 | 9/1986 | Goldberg | 436/147 |
| 4,677,841 | 7/1987 | Kennedy | 73/30 |
| 4,829,831 | 5/1989 | Kefer et al. | 73/861.02 |
| 4,845,976 | 7/1989 | Johnson et al. | 73/23 |
| 5,016,482 | 5/1991 | Clingman et al. | 73/863 |
| 5,201,581 | 4/1993 | Heyden et al. | 374/36 |
| 5,226,728 | 7/1993 | Heyden | 374/36 |

FOREIGN PATENT DOCUMENTS

| | | | |
|---|---|---|---|
| 0864113 | 2/1971 | Canada | 73/196 |
| 0326494 | 8/1989 | European Pat. Off. | 374/37 |
| 1110893 | 7/1961 | Fed. Rep. of Germany | 73/196 |
| 2099589 | 12/1982 | United Kingdom | 374/36 |

Primary Examiner—Richard E. Chilcot, Jr.
Assistant Examiner—Harshad Patel

[57] ABSTRACT

A method an apparatus for measuring a base condition volumetric flowrate of a pipeline gas flowing through a pipeline in which a pipeline gas flowrate is measured by a pipeline gas flowmeter; a volumetric correction ratio is derived by: measuring a sample gas flowrate of sample gas tapped from the pipeline, measuring an energy flowrate of the sample gas, measuring a heating value of the sample gas, and measuing a base condition density of the sample gas; and the base condition volumetric flowrate of the pipeline gas flowing through the pipeline is determined by adjusting the pipeline gas flowrate as measured by the pipeline gas flowmeter by the volumetric correction ratio. The temperature of the sample gas should be substantially the same as the pipeline gas in the pipeline when the sample gas flowrate is measured.

24 Claims, 6 Drawing Sheets

VOLUMETRIC FLOW CORRECTOR HAVING A DENSITOMETER

FIELD OF THE INVENTION

The present invention relates to the real time measurement of mass and energy flowrates through a pipeline. In particular, the invention relates to an apparatus and method for measuring a volumetric correction ratio which can be defined as a flowing condition density $\rho_f$ of a pipeline gas flowing through a pipeline compared to a base condition density $\rho_b$ of the pipeline gas. A volumetric correction ratio can be used to adjust a measured pipeline gas volumetric flowrate $Q_f$ into a corresponding base condition volumetric flowrate $Q_b$.

BACKGROUND OF THE INVENTION

In gaseous flows, the phenomena of compression exists and has a large effect. It allows the number of molecules for a given volume to change with pressure and temperature as well as with composition. Therefore, it is desirable to make natural gas sales transactions either by mass, energy, or at standard pressure and temperature conditions. In the U.S., for example, the standard pressure and temperature of gas is stated as 14.7 psia and 60° F. for many transactions. Delivery calculations state the flow adjusted to correspond to these base conditions even though the actual gas in the transaction is probably at a different pressure or temperature. A piece of equipment designed to accomplish the task of converting a measured volumetric flowrate $Q_f$ to a base volumetric flowrate $Q_b$ at a defined pressure and temperature is referred to as a "volume corrector".

In the traditional method of gas measurement, a volume correction ratio $$\frac{Q_b}{Q_f}$$

is determined from the pipeline gas flow temperature, pressure, and composition using the following relation:

$$\frac{Q_b}{Q_f} = \frac{T_b}{T_f} \frac{P_f}{P_b} \frac{Z_b}{Z_f} \quad (1)$$

where $Q_f$ is the measured volumetric flowrate of the pipeline gas through the pipeline, $T_b$ and $P_b$ are the base condition temperature and pressure (e.g. 14.7 psia and 60° F.), $T_f$ and $P_f$ are the measured flow temperature and pressure of the pipeline gas in the pipeline, $Z_b$ and $Z_f$ are the supercompressibility factors at the base condition and the flow condition, respectively, and $Q_b$ is the base condition volumetric flowrate. Such a calculation is typically carried out in a flow computer.

Using the relation in Eq. (1) to compute base condition volumetric flowrate $Q_b$ requires high accuracy in the measurement of the flow temperature $T_f$ and pressure $P_f$. This requires that pressure and temperature sensors for monitoring $P_f$ and $T_f$ be calibrated frequently.

The ratio $$\frac{Z_b}{Z_f}$$

in Eq. (1) presents even more difficulties. The composition of the gas is normally measured by gas chromatography and the supercompressibilities, $Z_b$ and $Z_f$, are estimated from either the virial equations of state, or from pre-calculated correlations such as NX-19 or the more recent Gergg Equations. Alternatively, a meter that measures heating value, relative density, $\%CO_2$ and $\%N_2$ can be used to calculate the ratio $$\frac{Z_b}{Z_f}.$$

This is because the Gergg Equations in their short form allow calculation of the ratio $$\frac{Z_b}{Z_f}$$

from these parameters.

Knowledge of the values of the virial coefficients of particular gas compositions is quite limited so calculation of supercompressibility from the virial equation of state is not always possible. The Gergg Equations and NX-19 correlation are mathematical models obtained by mapping known and measured properties. The Gergg Equations, in particular, are very good over a wide range of compositions. Use of the Gergg Equations, however, requires either a chromatograph or a special meter to measure the properties needed to solve the short form Gergg Equations, both of which are expensive.

It is, therefore, difficult to obtain accurate measurement of the supercompressibility ratio $$\frac{Z_b}{Z_f}$$

in a cost effective manner.

In U.S. Pat. No. 5,201,581, patented Apr. 13, 1991; U.S. Pat. No. 5,226,728, patented Jul. 13, 1993, and U.S. patent application Ser. No. 08/009,481, filed Jan. 25, 1993; Vander Heyden and Clingman disclose other inventions that can determine a volumetric flow correction ratio. These inventions by Vander Heyden and Clingman alleviate the need to compute supercompressibility when determining a volumetric flow correction ratio for a pipeline gas. These inventions also alleviate the need to measure the absolute temperature, absolute pressure, and composition of the pipeline gas. They can do this by tapping sample gas from a pipeline, maintaining the temperature of the sample gas at substantially the same temperature as the pipeline gas flowing through the pipeline, and measuring the flowrate of the sample gas or its equivalent while the sample gas is being maintained at substantially the same temperature as the pipeline gas. These inventions by Vander Heyden and Clingman operate accurately to determine energy flowrates, volume correction ratios $$\frac{Q_b}{Q_f},$$

and adjusted or base condition volumetric flowrates $Q_b$.

The inventions by Vander Heyden and Clingman referred to above require, however, that the sample gas flowmeter respond to density and density effects in the same manner as the pipeline gas flowmeter. This means that a volumetric flow corrector having a differential pressure sample gas flowmeter (such as a capillary with a differential pressure cell) which is made to be used with a differential pressure pipeline gas flowmeter (such as an orifice meter) cannot be used in another application where the pipeline gas meter is a linear flowmeter (such as a turbine meter). The flexibility of such a volumetric flow corrector is thus limited The same is also true for a volumetric flow corrector having a linear sample gas flowmeter.

The present invention can be used in conjunction with either a differential pressure pipeline gas flowmeter or a linear pipeline gas flowmeter. At the same time, it continues to alleviate the need to compute the supercompressibility of the pipeline gas, and also the need to measure the absolute temperature, the absolute pressure, and composition of the pipeline gas.

SUMMARY OF THE INVENTION

The present invention is a method and apparatus for measuring a volumetric flow correction ratio wherein a density of the sample gas at base conditions is measured. By measuring the density of the sample gas at base conditions, the invention is able to determine a volumetric flow correction ratio without requiring that a sample gas flowmeter respond to density and the effects of density in the same manner as a pipeline gas flowmeter with which it is used.

In one aspect, the present invention is a method for measuring a base condition volumetric flowrate ($Q_b$) of a pipeline gas flowing through a pipeline which corresponds to a volumetric flowrate at a base condition pressure and temperature. The method involves measuring a flowrate ($Q_f$) of a pipeline gas flowing through the pipeline with a pipeline gas flowmeter, determining a volumetric correction ratio, and adjusting the flowrate ($Q_f$) of the pipeline gas as measured by the pipeline gas flowmeter by the volumetric correction ratio. In one embodiment, the volumetric correction ratio is determined by flowing sample gas from the pipeline to a capillary, measuring a pressure drop of the sample gas across the capillary as the sample gas flows through the capillary, measuring an energy flowrate (energy per unit time) of the sample gas, measuring a heating value (energy per unit volume) of the sample gas, measuring a base condition density of the sample gas, and calculating the volumetric correction ratio from the measured pressure drop, energy flowrate, heating value, and density. The measured energy flowrate, heating value, and base condition density are each equivalent to what they would be if the sample gas were at base condition temperature and pressure. In a preferred form, a reference gas can be used to measure the base condition energy flowrate, heating value, and density without requiring the sample gas to be at base condition temperature and pressure.

The temperature of the sample gas should be maintained at substantially the same temperature as the pipeline gas when the sample gas is flowing through the capillary. After the sample gas has flowed through the capillary, it is no longer necessary to maintain the temperature of the sample gas at substantially the same temperature as the pipeline gas in the pipeline.

In another embodiment, the volumetric correction ratio is determined by flowing the sample gas from the pipeline to a linear sample gas flowmeter, measuring a sample gas flowrate with the linear sample gas flowmeter, measuring an energy flowrate (energy per unit time) of the sample gas, measuring a heating value (energy per unit volume) of the sample gas, measuring a base condition density of the sample gas, and calculating the volumetric correction ratio from the sample gas flowrate, the energy flowrate, the heating value, and the density. The temperature of the sample gas should be maintained at substantially the same temperature as the pipeline gas in the pipeline when the sample gas flowrate is being measured by the linear sample gas flowmeter.

In another aspect, the present invention is a volumetric flow corrector having a conduit for flowing sample gas from a pipeline; a sample gas flowmeter to measure the flowrate of the sample gas through the conduit, a sample gas energy flowmeter for measuring an energy flowrate (energy per unit time) of the sample gas flowing through the conduit; a sample gas heating value meter for measuring a heating value (energy per unit volume) of the sample gas flowing through the conduit; and a densitometer for measuring a base condition density of the sample gas. Signals from each of these meters can be transmitted to a control system where a volumetric correction ratio can be calculated. It is preferred that the densitometer comprise a chamber, a valve for controlling the flow of sample gas to the chamber, a flow restrictor for restricting the flow of sample gas from the chamber, a pressure sensor for measuring the pressure in the chamber, a means for determining a time rate of change of pressure in the chamber as the sample gas flows through the flow restrictor, and a reference gas. With this kind of densitometer, the density of the sample gas flowing to the sample gas energy flowmeter and sample gas heating value meter can be derived as proportional to the inverse of the square of the time rate of change of pressure in the chamber, and comparing that value to a value obtained in the same manner for the reference gas.

The sample gas flowmeter in the volumetric flow corrector is preferably a linear flowmeter in one embodiment and a differential pressure flowmeter in another embodiment. In the embodiment having a sample gas differential pressure flowmeter, it is preferred that the meter comprise of a capillary and a differential pressure cell to measure the pressure drop of sample gas flowing through the capillary.

The general object of the present invention is to allow accurate measurement of energy flowrates, volume correction ratios $$\frac{Q_b}{Q_f}$$

and adjusted volumetric flowrates $Q_b$ (i.e., base condition volumetric flowrates) in an improved manner. The present invention improves the accuracy of these measurements because it alleviates the need to consider the effects of the supercompressibility, temperature, pressure, or composition. It can do this because the critical measurement (i.e., the sample gas volumetric flowrate $Q_f$) is made when the sample gas is at a condition related to pipeline conditions.

An advantage of the present invention is that it is extremely accurate. This is, in part, because the measurement of the sample gas heating value and energy flowrate can be made very accurately because the relation between the amount of air and the paraffin gas energy content when combusted at maximum flame temperatures is accurate within 0.1%. Another reason is that the present invention allows intermittent referencing from a reference gas to insure that the measurement of the sample gas heating value $H_{sample\ gas}$ is accurate and does not drift.

Another object of the present invention is to monitor the pipeline gas without substantially disrupting the flow of pipeline gas through the pipeline. The present invention achieves this object by deriving the volume correction ratio $$\frac{Q_b}{Q_f}$$

or other results by tapping sample gas from the pipeline and making measurements on the sample gas at a location isolated from the pipeline.

Yet another object of the present invention is to provide a volumetric flow corrector that is able to be used with both differential pressure pipeline flowmeters and linear pipeline flowmeters.

The foregoing and other objects and advantages of the present invention will appear from the following description. In the description, references are made to the accompanying drawings which form a part hereof and in which preferred embodiments of the present invention are shown by way of illustration. Such embodiments do not necessarily represent the full scope of the invention.

DESCRIPTION OF THE PREFERRED EMBODIMENT

Figure 1:
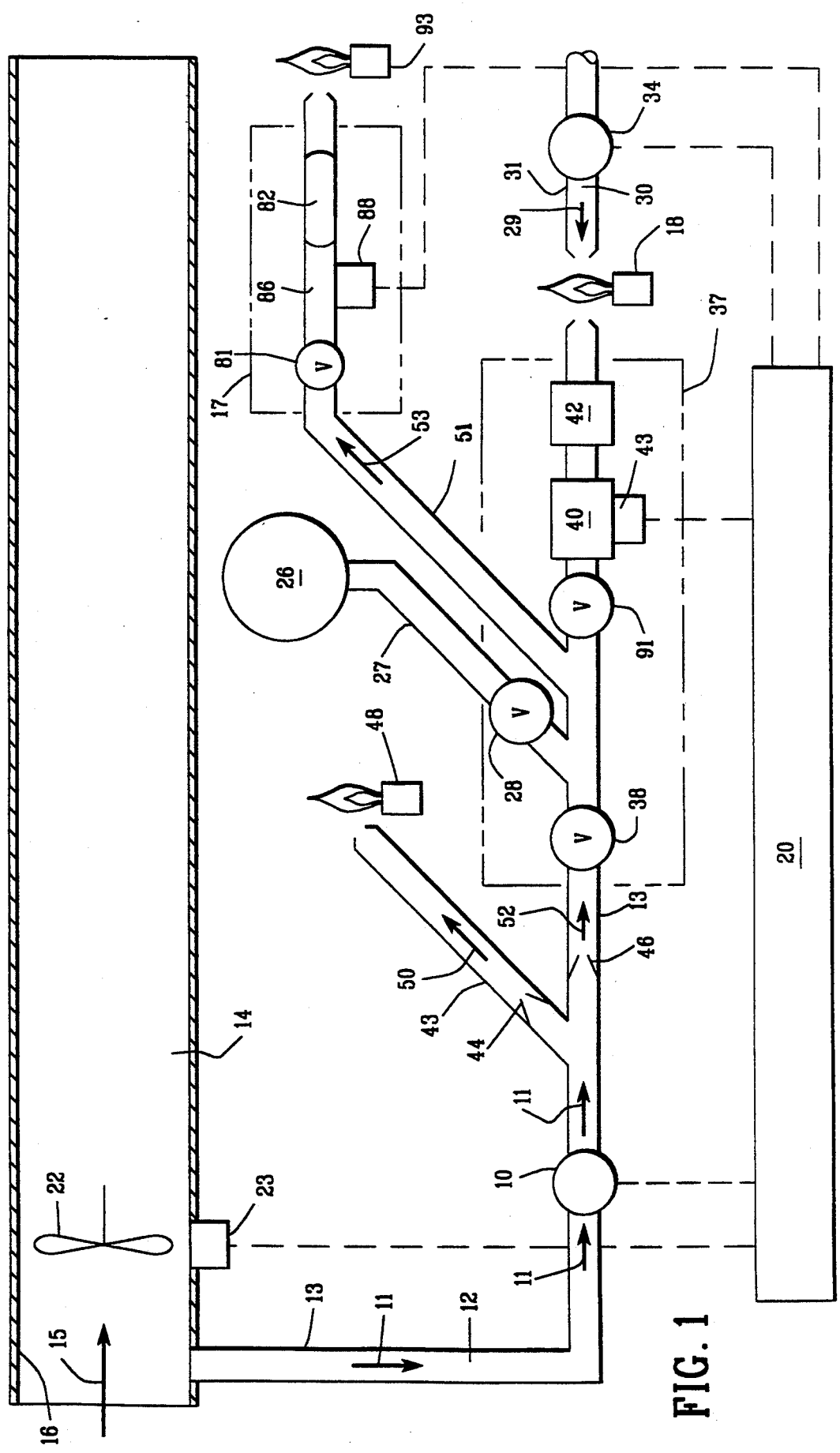
FIG. 1 is a schematic drawing illustrating the apparatus of the present invention.
Figure 7:
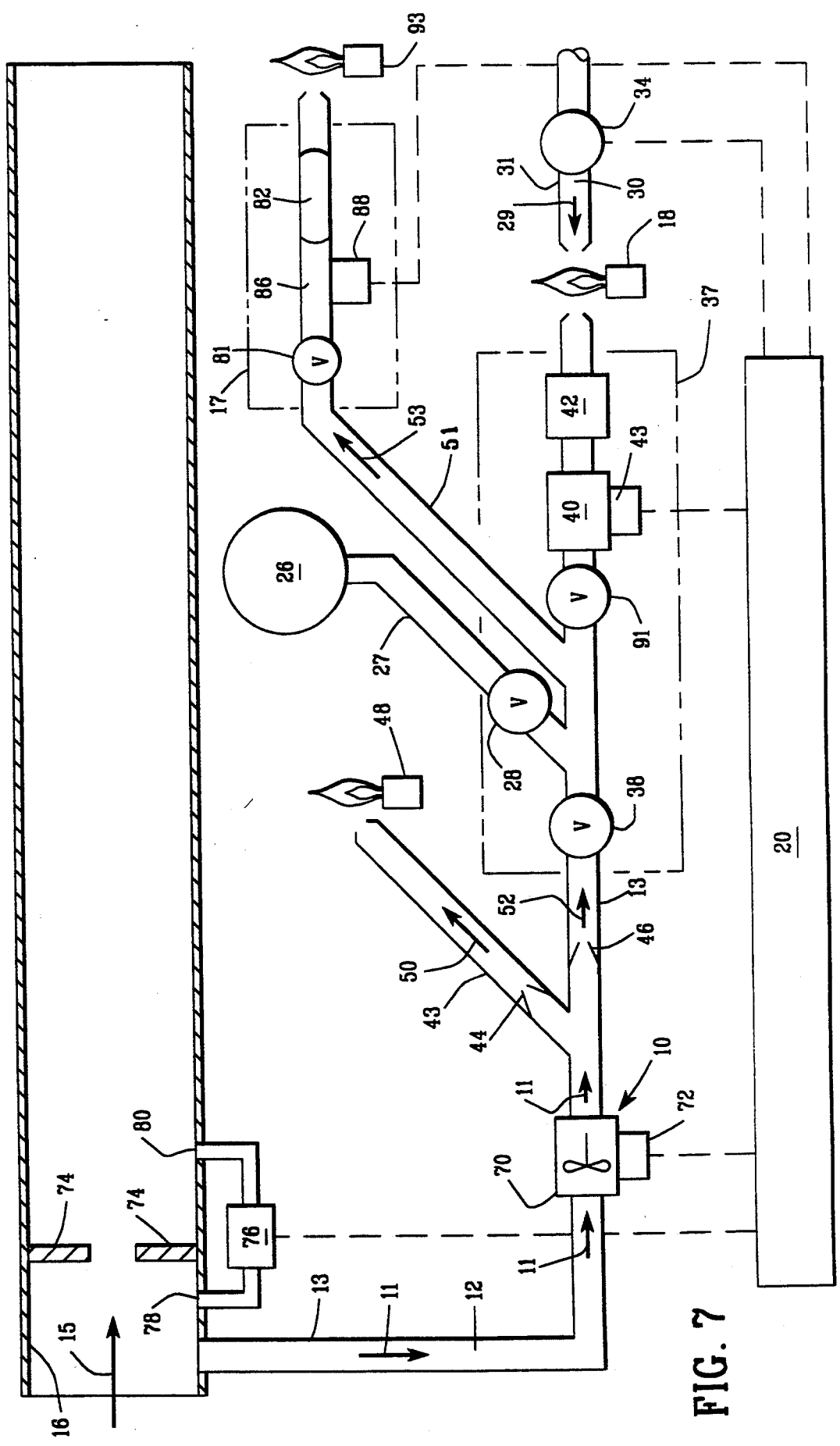
FIG. 7 is a schematic drawing similar to FIG. 1 in which a sample gas flowmeter is a turbine flowmeter.

Referring to FIG. 1, the apparatus of the present invention is used in conjunction with a pipeline gas 22 flowmeter that measures a flowrate $Q_f$ of a pipeline gas 14 flowing through a pipeline 16 in the direction of arrow 15. The measured pipeline gas flowrate $Q_f$ is typically a volumetric flowrate. In FIG. 1, the pipeline gas flowmeter is depicted as a turbine flowmeter 22, but the pipeline gas flowmeter need not be a turbine flowmeter 22. It may be another type of flowmeter, including a differential pressure flowmeter, as shown in FIG. 7.

The apparatus of the present invention can be thought of generally as a sample gas meter 10 for measuring a flowrate $Q_f'$ of sample gas 12 flowing through a conduit 13 in the direction of arrow 11, where the sample gas 12 is tapped from the flow of pipeline gas 14 through the pipeline 16; a sample gas energy detector 18 for monitoring a sample gas energy flowrate (energy/time) $E_{sample\ gas}$ and for monitoring a sample gas heating value (energy/volume) $H_{sample}$ gas; a sample gas densitometer 17 for monitoring a base condition density $\rho_b$ of the sample gas 12; and a control system 20 for computing a base condition volumetric flowrate $Q_b$ for the pipeline gas 14 flowing through the pipeline 16.

The control system 20 computes the pipeline gas base condition volumetric flowrate $Q_b$ from an electronic signal representing the pipeline gas flowrate $Q_f$ as measured by the pipeline gas flowmeter 22 and generated by a signal generator 23, a signal from the sample gas meter 10 representing the flowrate $Q_f'$ of the sample gas, a signal from the gas densitometer 17 representing the base condition density $\rho_b$ of the sample gas 12 and signals from a sample gas burner flow adjuster or meter 37 (collectively components 28, 38, 40, 42, and 43) and possibly from an air flowmeter 34 which represent $E_{sample\ gas}$ and $H_{sample\ gas}$.

In addition, the control system 20 can compute the energy flowrate (energy/time) of the pipeline gas 14 through the pipeline 16. The pipeline gas energy flowrate is easily calculated by multiplying the sample gas energy flowrate $E_{sample\ gas}$ by the ratio of $$\frac{Q_f}{Q_f'},$$

which is the ratio of the pipeline gas 14 flowrate $Q_f$, as measured by the pipeline gas flowmeter 22 in the pipeline 16, compared to the sample gas flowrate $Q_f'$ as measured by the sample gas flowmeter 10.

The base condition volumetric flowrate $Q_b$ for the pipeline gas 14 can be derived from the measured flowrate $Q_f$ of the pipeline gas by adjusting $Q_f$ to correspond to what the volumetric flowrate would be at defined base conditions, such as 60° F. and 14.7 psi. The American Gas Association has set standards for both linear and orifice volumetric meters to determine the volume correction ratio $$\frac{Q_b}{Q_f}$$

used to derive an adjusted or base condition volumetric flowrate $Q_b$ from a measured flowrate $Q_f$. The AGA relation may be stated as:

$$\frac{Q_b}{Q_f} = \left( F_{Pf} F_{Pb} F_{Tf} F_{Tb} \frac{Z_b}{Z_f} \right) \tag{2}$$

where $F_{Pf}$ is a pressure factor at flow conditions, $F_{Pb}$ is a pressure factor at base conditions, $F_{Tf}$ is a temperature factor at flow conditions, $F_{Tb}$ is the temperature factor at base conditions, and the ratio $$\frac{Z_b}{Z_f}$$

is the ratio of the compressibility factor at base conditions to the compressibility factor at flow conditions. The present invention alleviates the need to use a relation such as Eq. (2).

In the present invention, the volume correction ratio $$\frac{Q_b}{Q_f}$$

for a pipeline gas 14 flowing through a pipeline 16 is equivalent to a volume correction ratio $$\frac{Q_b'}{Q_f'}$$

for sample gas 12 tapped from the pipeline 16. That is:

$$\frac{Q_b}{Q_f} = \frac{Q_b'}{Q_f'} \qquad (3)$$

The relation in Eq. (3) is true if the temperature, pressure, and composition of the gas flowing through the sample gas flowmeter 10 is substantially the same as the temperature, pressure, and composition of the pipeline gas 14 flowing through the pipeline 16. The pressure and the composition of the sample gas 12 are substantially the same as the pressure and the composition of the pipeline gas 14 flowing through the pipeline 16 because the sample gas 12 flowing to the sample gas flowmeter 10 is tapped directly from the pipeline 16.

Figure 2:
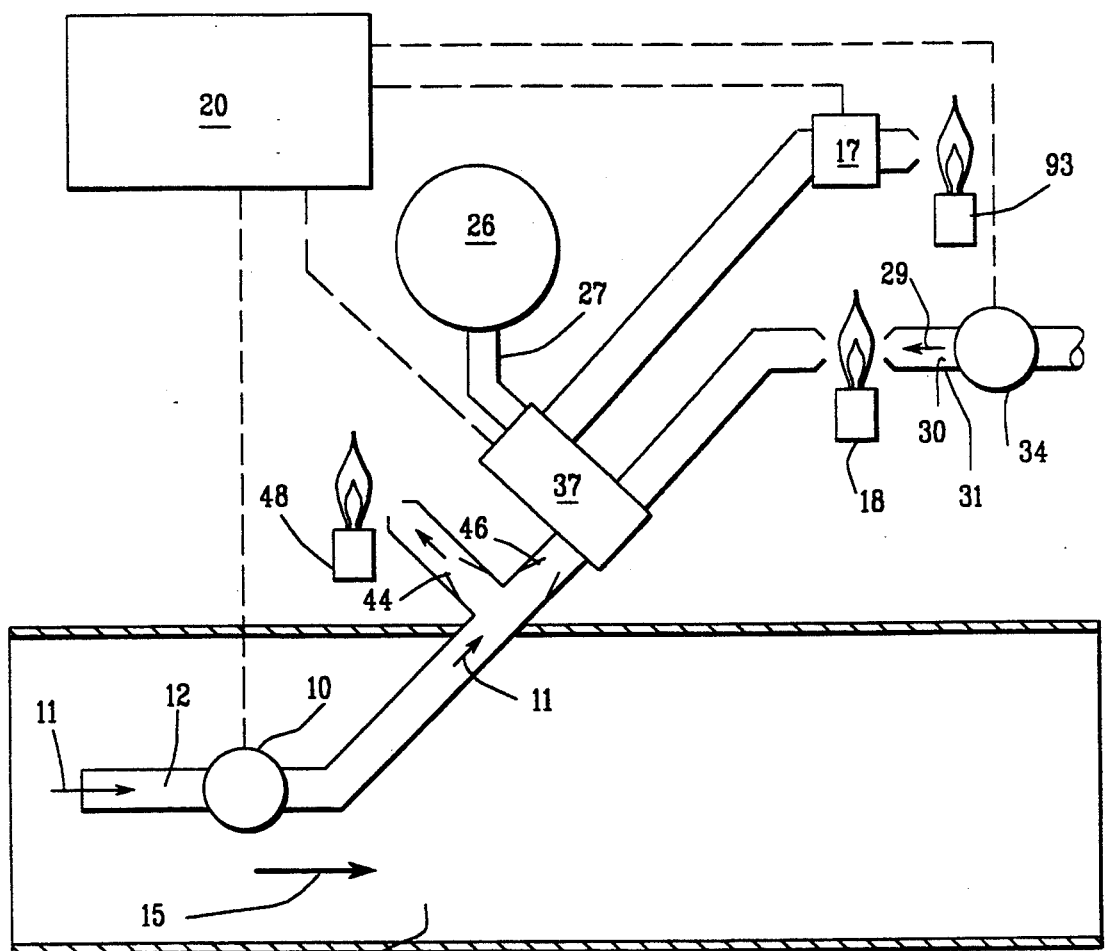
FIG. 2 is a schematic drawing showing a sample gas flowmeter residing within a pipeline gas flow in a pipeline.

Referring to FIG. 2, the temperature of the sample gas 12 can be maintained at substantially the same temperature as the pipeline gas 14 by immersing the sample gas flowmeter 10 into the stream of pipeline gas 14 flowing through the pipeline 16. Alternatively, referring to FIG. 3, the sample gas 12 can be maintained at substantially the same temperature as the pipeline gas 14 flowing through the pipeline 16 by routing the sample gas 12 to a sample gas flowmeter 10 through a longer serpentined conduit 24 where both the serpentined conduit 24 and the sample gas flowmeter 10 are mounted in intimate contact with the outside surface of the pipeline 16. Insulation 25 should be placed around the serpentined conduit 24, the sample gas flowmeter 10 and the pipeline 16 to facilitate temperature equalization.

Figure 3:
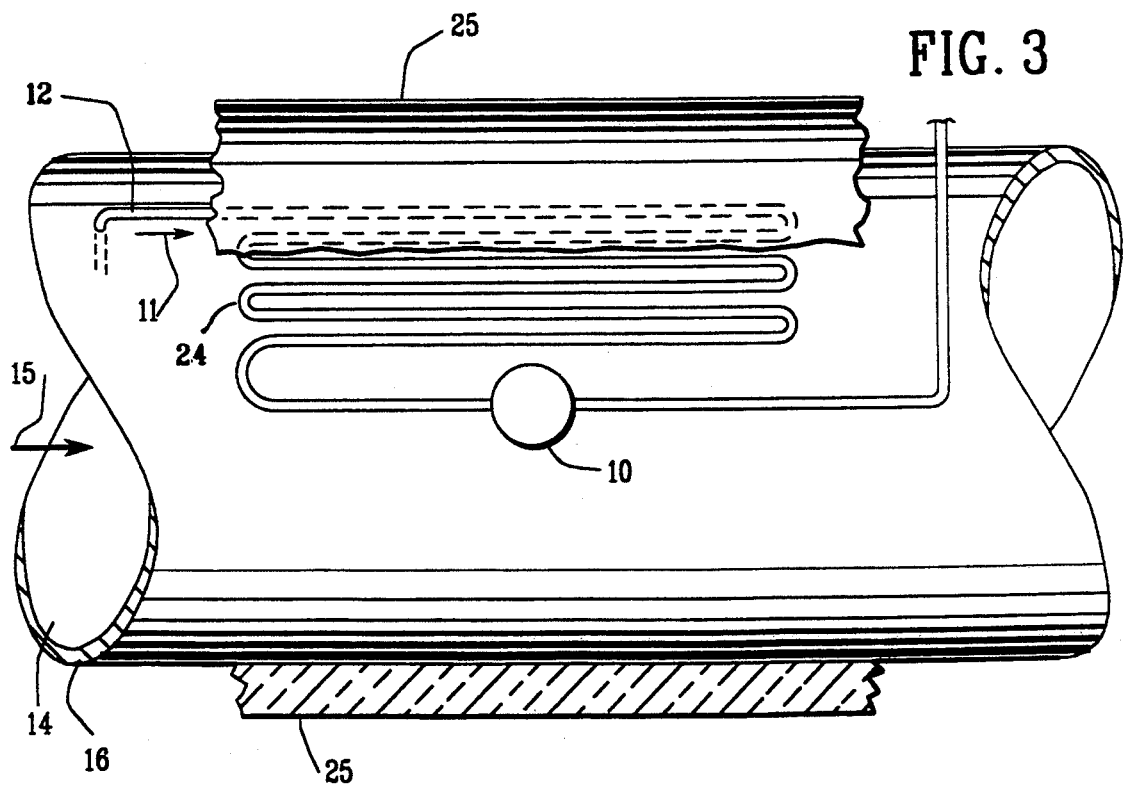
FIG. 3 is a schematic drawing showing a sample gas flowmeter being mounted in intimate contact with a pipeline.

With either the configuration shown in FIG. 2 or the configuration shown in FIG. 3, the temperature of the sample gas 12 within the sample gas flowmeter 10 can be maintained at substantially the same temperature as the temperature of the pipeline gas 14 flowing through the pipeline 16. Under these conditions, Eq. (3) applies and the volume correction ratio for the sample gas $$\frac{Q_b'}{Q_f'}$$

can be measured and used to adjust the pipeline gas 14 flowrate $Q_f$ as measured by the pipeline gas flowmeter 22 to derive the pipeline gas base condition volumetric flowrate $Q_b$ as shown by the following relation:

$$Q_b = Q_f \left( \frac{Q_b'}{Q_f'} \right) \qquad (4a)$$

or upon rearranging:

$$Q_b = Q_{b'} \left( \frac{Q_f}{Q_{f'}} \right). \qquad (4b)$$

Determination Of The Sample Gas Base Condition Volumetric Flow $Q_b'$

Referring generally to FIG. 1, the sample gas base condition volumetric flowrate $Q_b'$ is measured by energy methods as described by the following relation:

$$Q_b' = \frac{E_{sample\ gas}}{H_{sample\ gas}} \qquad (5)$$

where $E_{sample\ gas}$ is the base condition energy flowrate of the sample gas 12 through the sample gas flowmeter 10 (energy/time) and $H_{sample\ gas}$ is the base condition heating value of the sample gas 12 flowing through the sample gas flowmeter 10 (energy/volume). The base condition energy flowrate $E_{sample\ gas}$ and the heating value $H_{sample\ gas}$ of the sample gas 10 are determined by flowing the sample gas 12 to the burner 18 and burning the sample gas 12 with air 30 which is also flowed to the burner 18 in the direction of arrow 29.

Referring to FIG. 1, the sample gas 12 stream can be split using parallel sonic nozzles 44 and 46 after the sample gas 12 flows from the sample gas flowmeter 10. Such a system may be useful when it is desired to flow more sample gas 12 through the sample gas flowmeter 10 than to the burner 18. In such a system, sonic nozzle 44 is located in line 43 and sonic nozzle 46 is located in line 13 leading to the burner 18. In FIG. 1, line 43 leads to a catalytic burner 48, but line 43 could lead to another waste method.

Since the temperature, pressure, differential pressure, and composition of the sample gas 12 flowing to the sonic nozzles 44 and 46 is the same, the mass flow of sample gas 12 flowing from the sample gas flowmeter 10 can be split in a known ratio into a waste stream shown by arrow 50 flowing through line 43 and a test stream shown by arrow 52 flowing to the burner 18 and associated apparatus. The ratio of the mass flowrate $\omega_s$ of the sample gas 12 flowing through the sample gas flowmeter 10 to the mass flowrate $\omega_b$ of the sample gas 12 flowing to the burner 18 is designated herein as a split ratio S. The energy flowrate $E_{sample\ gas}$ of the sample gas can be determined by multiplying the energy flowrate as determined by burning the sample gas 12, by the split ratio S. The sonic nozzles 44 and 46 can generally be thought of as a flow splitter.

Reference can be made to U.S. Patent Nos. 3,777,562; 4,062,236; 4,125,018; and 4,125,123, all issued to Clingman, which describe how the heating value and the energy content of the sample gas 12 can be measured. In brief, the amount of air 30 required to completely combust a saturated hydrocarbon gas (e.g., sample gas 12 flowing to the burner 18) at a maximum flame temperature is proportional to the energy released during combustion. In fact, the energy flowrate of a saturated hydrocarbon gas is related to the air 30 flowrate $\omega_{air}$ through a constant $K_{max}$ which has a known and constant value for all saturated hydrocarbon gases, with or without inert fractions. If inert gases are mixed with the fuel, the temperature of the flame reduces due to inert cooling, however, at the maximum temperature for the fuel mixture, the relation between the heating value and the fuel-air ratio remains absolute. Also, $K_{max}$ remains accurate even with mixtures of gas containing small fractions of non-paraffinic gases such as hydrogen.

Figure 4A:
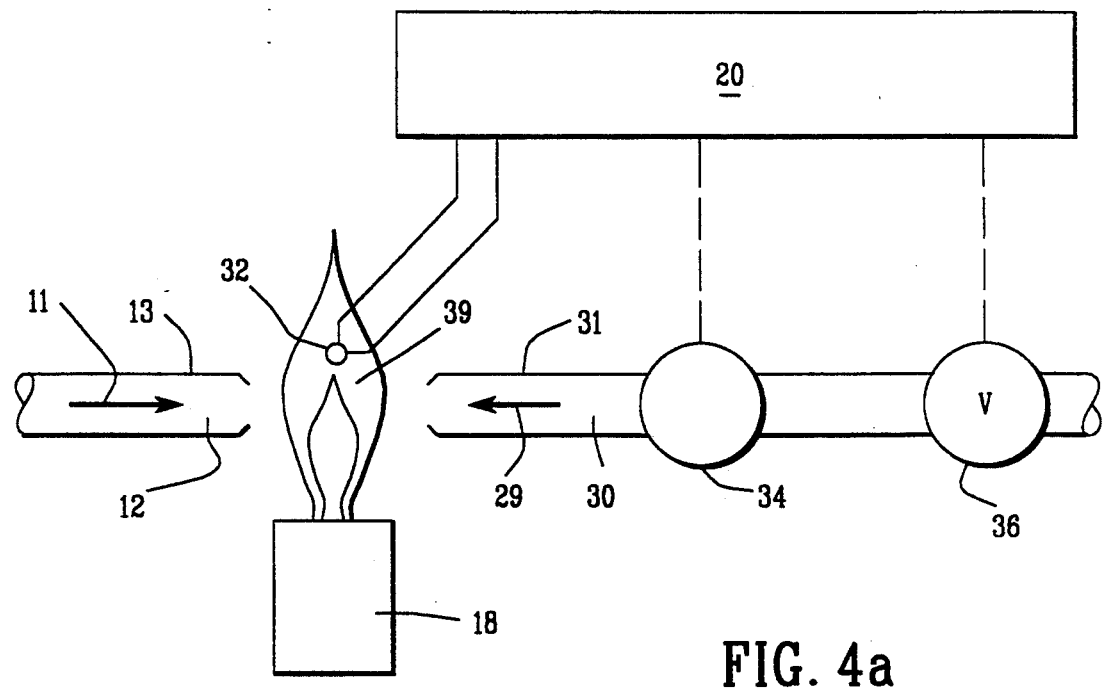
FIGS. 4a and 4b are schematic drawings showing apparatus for measuring the energy flowrate and heating value of the sample gas.

Using this stoichiometric method, the base condition energy flowrate $E_{burner}$ of the sample gas 12 flowing to the burner 18 can be represented by:

$$E_{burner} = K_{max} \omega_{air} \qquad (6)$$

where $K_{max}$ is the stoichiometric proportionality constant, and $\omega_{air}$ is the air mass flowrate to the burner 18. Referring in particular to FIG. 4a, sample gas 12 flows to the burner 18 after it flows from the sample gas flowmeter 10 and possibly other apparatus which is described below. Air 30 is supplied to the burner 18 in the direction of arrow 29 through an air hose 31. The sample gas 12 burns with the air 30 above the burner 18 to form a flame 39. A thermocouple 32 monitors the flame 39 temperature and communicates to the control system 20. Air 30 flowing through the air hose 31 is monitored by an air mass flowmeter 34. Air mass flowmeters are old in the art and are accurate in ambient conditions. The air flow 30 is adjusted by an air valve 36, which is controlled by the control system 20, until the sample gas 12 burns at maximum flame temperature. When the flame burns at the maximum flame temperature, the base condition sample gas energy flowrate $E_{sample\ gas}$ can be determined from a signal from the air flowmeter 34 using Eq. (6).

While an air mass flowmeter 34 is the preferred way of measuring the air mass flowrate $\omega_{air}$, a volumetric or a molar flowmeter can be used. Note, also, that the base condition sample gas energy flowrate $E_{sample\ gas}$ can be measured by flowing a constant air mass flowrate $\omega_{air}$ to the burner 18 and adjusting a flowrate $Q'_{burner}$ of sample gas 12 to the burner 18 until maximum flame temperature is achieved. When maximum flame temperature is achieved, the base condition energy flowrate $E_{burner}$ of sample gas 12 to the burner 18 can again be determined from Eq. (6).

Figure 4B:
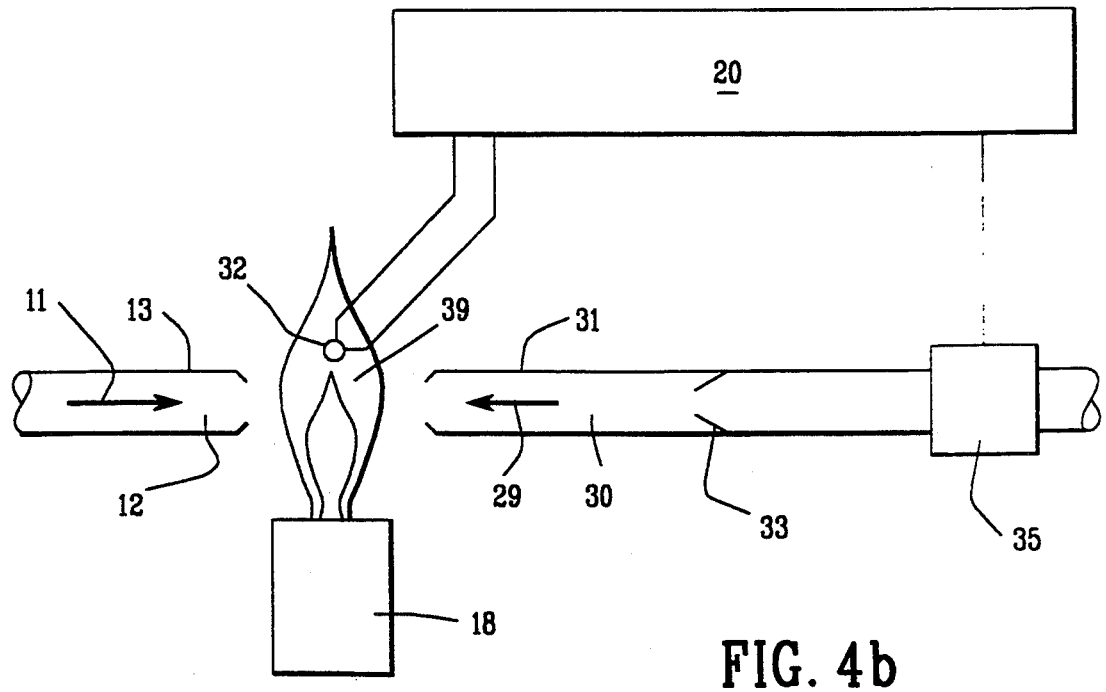

One way to flow air to the burner 18 at a constant flowrate is to flow air through a sonic nozzle under critical flow conditions. Referring to FIG. 4b, such an air system is composed of a very accurate pressure controller 35 forcing air into a sonic nozzle 33. The resulting air flow 30 burns with sample gas 12 in the burner 18. It is preferred that the pressure controller 35 communicate with the control system 20 so the air flowrate $\omega_{air}$ be known in the control system 20. The use of the sonic nozzle 33 under critical flow conditions results in long-term air flow stability. The number of oxygen molecules forced to combustion is very stable. The air flow 30 through the sonic nozzle 33, assuming critical pressure is exceeded, is described as:

$$\omega_{air} = \frac{K_{air} P_{air}}{T_{air}} \qquad (7)$$

where $K_{air}$ is the nozzle 33 constant for air, $P_{air}$ is absolute pressure at the nozzle 33 inlet and $T_{air}$ is the absolute temperature at the nozzle 33 inlet. If air pressure $P_{air}$ is maintained constant, the air flow 30 to the burner 18 is constant, and the sample gas energy flowrate to the burner 18 ($E_{burner}$) can remain constant by adjusting the flowrate ($Q'_{burner}$) of sample gas 12 to the burner 18. Referring to FIG. 1, the sample gas 12 flowrate $Q'_{burner}$ to the burner 18 can be measured using a solenoid valve 38, a volume chamber 40, and a flow controller 42 in the conduit 13 as the sample gas 12 flows to the burner 18. Such a volumetric or molar flowmeter for measuring the flowrate $Q'_{burner}$ of sample gas 12 to the burner 18 is described in U.S. Pat. 4,285,245, issued Aug. 25, 1981, by Kennedy. This is the preferred way to adjust and measure $Q'_{burner}$, but other ways are known in the art and are acceptable.

A reference gas 26 with a known heating value at base conditions $H_{reference\ gas}$ is used to determine the base condition heating value of the sample gas $H_{sample\ gas}$. Methane is a suitable reference gas 26. At U.S. base conditions of 60° F. and 14.7 psi, methane has a heating value of about 1,014 Btu/standard cubic foot. In general, the base condition sample gas heating value $H_{sample\ gas}$ can be determined by intermittently flowing the reference gas 26 to the burner 18 and measuring flowrate. Using a reference gas 26 allows the base condition sample gas heating value $H_{sample\ gas}$ to be determined without measuring ambient temperature and pressure.

The energy flowrate of the sample gas flowing to the burner can be represented as the sample gas heating value $H_{sample\ gas}$ (energy per unit volume) multiplied by the sample gas volumetric flowrate to the burner $Q_{sample\ gas}$ (volume/time). Likewise, the energy flowrate of the reference gas flowing to the burner can be represented as the reference gas heating value $H_{reference\ gas}$ multiplied by the reference gas volumetric flowrate to the burner $Q_{reference\ gas}$. Also, from Eq. (6), it can be seen that the ratio of the energy flowrate of the sample gas flowing to the burner compared to the energy flowrate of the reference gas flowing to the burner is the ratio $\omega_{air\ sample}/\omega_{air\ reference}$ where $\omega_{air\ sample}$ is the air flowrate to the burner when the sample gas is being burned at maximum flame temperature, and $\omega_{air\ reference}$ is the air flowrate to the burner when the reference gas is being burned at maximum flame temperature. The base condition sample gas heating value $H_{sample\ gas}$ can therefore be generally represented by:

$$H_{sample\ gas} = H_{reference\ gas} \left( \frac{Q_{reference\ gas}}{Q_{sample\ gas}} \right) \left( \frac{\omega_{air\ sample}}{\omega_{air\ reference}} \right) \qquad (8)$$

Referring still to FIG. 1, a reference gas 26 can be hooked-up via line 27 and valve 28 to use volume chamber 40 and flow controller 42 for measuring the flowrate of a reference gas 26 flowing to the burner 18. As is described in U.S. Pat. No. 4,285,245, flowrate can be measured by determining the rate of pressure decay in chamber 40. For instance, to measure the flowrate $Q_{sample\ gas}$ of the sample gas 12 flowing to the burner 18, valves 38 and 91 are opened, valves 28 and 81 are closed, and volume chamber 40 is allowed to fill with sample gas 12. Valve 91 is then closed and the time rate of change of pressure in volume chamber 40 is determined as the sample gas 12 within volume chamber 40 flows through the flow controller 42 to the burner 18. To measure the flowrate $Q_{reference\ gas}$ of reference gas 26 flowing to the burner 18, valves 38 and 81 are closed and valves 28 and 91 are opened so that the chamber 40 can fill with reference gas 26. Then valve 91 is closed and the time rate of change of pressure in volume chamber 40 is measured as reference gas 26 flows to the burner 18.

Assuming that the air flow $\omega_{air}$ to the burner is constant between referencing and sampling periods, the sample gas heating value at base conditions (energy per unit volume) $H_{sample\ gas}$ can be determined from the following relation:

$$H_{sample\ gas} = \frac{\frac{\partial P}{\partial t_{reference\ gas}}}{\frac{\partial P}{\partial t_{sample\ gas}}} H_{reference\ gas} \quad (9)$$

where $$\frac{\partial P}{\partial t}$$

is the time rate of change of pressure in chamber 40 and $H_{reference\ gas}$ is the heating value at base conditions for the reference gas 26.

The following analysis explains the determination of $$\frac{\partial P}{\partial t}$$

in Eq. (9). The rate of pressure change in the chamber 40 with a constant molar flowrate therefrom (or controlled by flow controller 42) is:

$$\frac{\partial P}{\partial t}\left(\frac{V}{RT}\right) = Z\frac{\partial n}{\partial t} + n\frac{\partial Z}{\partial t} \quad (10)$$

where V is the volume of chamber 40, T is the temperature of gas in the chamber 40, R is a universal gas constant, n is the amount of moles of gas in the chamber 40, $$\frac{\partial n}{\partial t}$$

is the time rate of change of the amount of moles in the chamber 40, Z is the supercompressibility factor for the gas in the chamber 40 and $$\frac{\partial Z}{\partial t}$$

is the time rate of change of Z as the gas flows from chamber 40. The time rate of change of Z can be expressed as:

$$\frac{\partial Z}{\partial t} = \frac{\partial P}{\partial t}\left(\frac{\partial Z}{\partial P}\right)_T \quad (11)$$

where $$\left(\frac{\partial Z}{\partial P}\right)_T$$

is the rate of change of Z with respect to pressure at constant temperature.

Substituting Eq. (10) into Eq. (11) and simplifying gives:

$$\frac{\partial P}{\partial t}\left(\frac{V}{RT}\right)\left[Z - P\left(\frac{\partial Z}{\partial P}\right)_T\right] = Z^2\frac{\partial n}{\partial t} \quad (12)$$

The supercompressibility of the gas Z can be written as a virial power series with pressure coefficients that are a function of temperature and composition only:

$$Z = 1 + b(T,x)P_m + c(T,x)P_m^2 + \ldots \quad (13)$$

where $P_m$ is the pressure at which Z is being computed and b(T,x) and c(t,x) are the second and third virial coefficients. Higher order terms can be neglected because of the relatively low pressures in chamber 40. Substituting Z and $$\left(\frac{\partial Z}{\partial P}\right)$$

into Eq. (13) and simplifying gives:

$$\frac{\partial P_m}{\partial t}\left(\frac{V_m}{RT}\right) = [1 + 2bP_m + (3c + b^2)P_m^2]\frac{\partial n}{\partial t} \quad (14)$$

Equation (14) shows that $$\frac{\partial P}{\partial t}$$

measurements are independent of molecular weight. Therefore, the heating value in Eq. (9) can be measured independent of molecular weight changes which could be due to composition changes. Substituting Eq. (14) into Eq. (9) gives the relation:

$$H_{sample\ gas} = \frac{\left(TZ'\frac{\partial n}{\partial t}\right)_{reference\ gas}}{\left(TZ'\frac{\partial n}{\partial t}\right)_{sample\ gas}} H_{reference\ gas} \quad (15)$$

where $Z'$ represent $[1+2bP_m+(3c+b^2)P_m^2]$. To solve for $H_{sample\ gas}$ in Eq. (15), the temperature of the sample gas 12 must be compared to the temperature of the reference gas 26 at the time of referencing. The temperature of the sample gas 12 is not compared to the base condition temperature.

Also, to solve for $H_{sample\ gas}$ in Eq. (15), the $Z'$ ratio of the sample gas 12 compared to the reference gas 26 must be determined. It is necessary to consider only the first and second terms in the $Z'$ expansion because relatively low pressures in chamber 40 make higher terms negligible. Eq. (15) then becomes:

$$H_{sample\ gas} = \frac{\left(T(1 + 2bP_m)\frac{\partial n}{\partial t}\right)_{reference\ gas}}{\left(T(1 + 2bP_m)\frac{\partial n}{\partial t}\right)_{sample\ gas}} H_{reference\ gas} \quad (16)$$

Equation (16) includes two "2bP" terms—one at the sample gas 12 conditions and one at the reference gas 26 conditions. The pressure $P_m$ at which the rate of change of pressure in chamber 40 is measured remains constant whether measuring sample gas 12 flowrate or reference gas 26 flowrate, so Eq. (16) can be reduced to:

$$H_{sample\ gas} = \frac{\left(T\frac{\partial n}{\partial t}\right)_{reference\ gas}}{\left(T\frac{\partial n}{\partial t}\right)_{sample\ gas}} (1 + 2\ (b_{sam} - b_{ref})P_m)H_{reference\ gas} \quad (17)$$

The importance of Eq. (17) is that the sample gas 12 heating value at base conditions $H_{sample\ gas}$ can be determined from the reference gas 26 heating value at base conditions $H_{reference\ gas}$ using Eq. (9), without any need to monitor temperature and pressure at the time the measurements are made. This is because 1) the ratio $$\frac{\left(\frac{dP}{dt}\right)_{reference\ gas}}{\left(\frac{dP}{dt}\right)_{sample\ gas}}$$

in Eq. (9) is inherently determined for the flow temperature of the reference gas 26, not for the standard temperature (e.g. 60° F.); and 2) the pressure in chamber 40 at which $$\left(\frac{dP}{dt}\right)_{sample\ gas} \text{ and } \left(\frac{dP}{dt}\right)_{reference\ gas}$$

are measured can be held constant. Therefore $H_{sample\ gas}$ can be determined from $H_{reference\ gas}$ regardless of the ambient conditions.

It is important to note that the above derivation for the sample gas 12 heating value $H_{sample\ gas}$ is made with one major assumption—that the air flow $\omega_{air}$ to the burner 18 (where maximum flame temperature is achieved) is absolutely constant between referencing and sampling periods. If the air flow were to change, Eq. (9) must be modified to $$H_{sample\ gas} = \frac{\frac{dP}{dt_{reference\ gas}}}{\frac{dP}{dt_{sample\ gas}}} \left(\frac{\omega_{air\ sample}}{\omega_{air\ reference}}\right) H_{reference\ gas} \quad (18)$$

Equation (18) shows that air flow to the burner 18 can be adjusted in lieu of adjusting gas flowrate or along with adjusting gas flowrate.

Measurement of The Ratio $$\left(\frac{Q_f}{Q_f'}\right)$$

In U.S. patent application Ser. No. 08/009,481, it is explained that the pipeline gas base condition volumetric flowrate $Q_b$ (i.e. $Q_b = Q_b'$ $$\left(\text{i.e. } Q_b = Q_{b'}\left(\frac{Q_f}{Q_f'}\right)\right)$$

can be measured without considering density or the effects of density, if the sample gas 10 flowmeter responds to density in the same manner as the pipeline gas flowmeter 22. In contrast to the invention disclosed in U.S. patent application Ser. 08/009,481, the present invention does not require that the sample gas flowmeter 10 respond to density in the same manner as the pipeline gas flowmeter 22. Rather, the present invention measures the base condition density $\rho_b$ of the sample gas.

The base condition density $\rho_b$ of the sample gas 12 can be measured by closing valve 91 and flowing sample gas 12, and reference gas 26 intermittently, to the densitometer 17. Gas 12 or 26 flows to the densitometer 17 through a conduit 51 in the direction of arrow 53. Gas 12 or 26 flowing from the densitometer 17 is catalytically burned by a catalytic burner 93. There are several types of gas densitometers known in the art which are suitable for measuring the base condition density $\rho_b$ of the sample gas 12. The preferred densitometer 17 is shown in FIG. 5.

Figure 5:
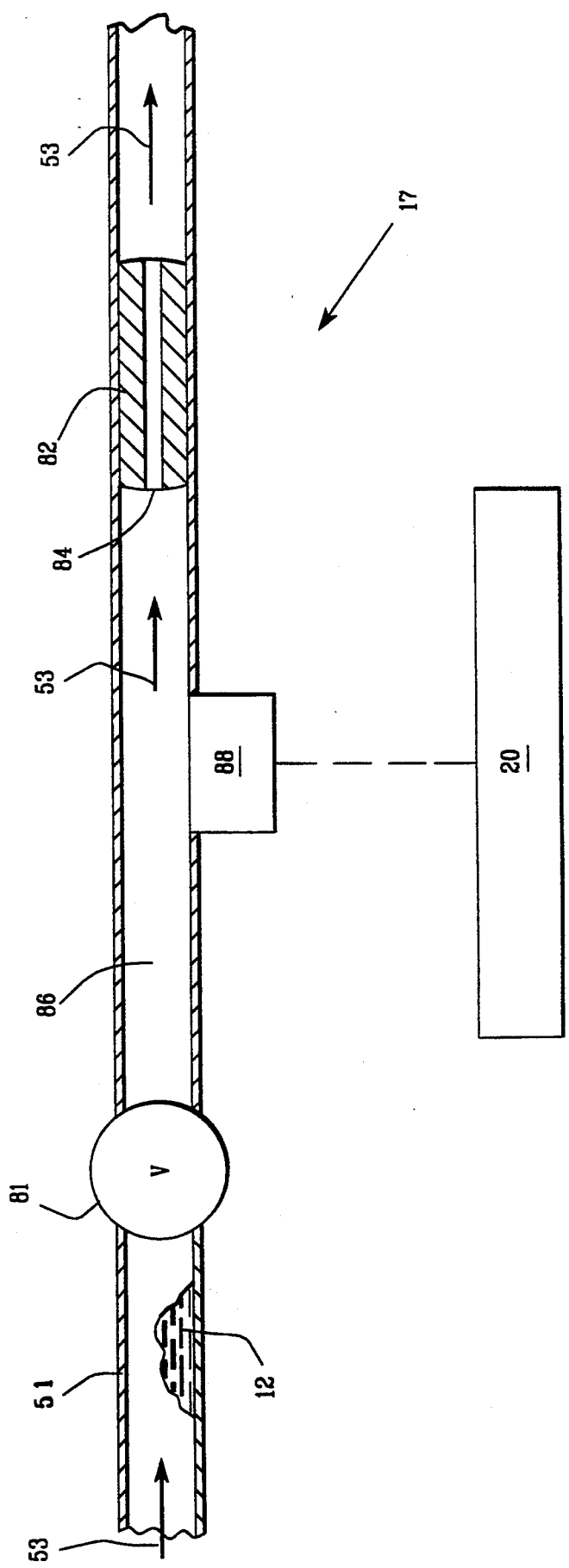
FIG. 5 is a schematic drawing of a densitometer used in the apparatus of the present invention.

The structure and operation of the densitometer 17 shown in FIG. 5 is described in U.S. Pat. No. 4,677,841, issued on Jul. 7, 1987 to Kennedy and entitled "Method and Apparatus for Measuring the Relative Density of Gases". The disclosure in U.S. Pat. No. 4,677,841 is incorporated herein by reference.

Referring to FIG. 5, the preferred densitometer 17 can generally be described as a valve 81 in line 51, a piece of sapphire 82 in line 51 with a pore 84 drilled therethrough, a volume 86 between the valve 81 and the piece of sapphire 82, and a pressure transducer 88 for measuring the pressure in the volume 86. The pore 84 is preferably a 0.002 inch diameter hole drilled through the piece of sapphire 82. The valve 81 can be opened to allow sample gas 12 to flow into the volume chamber 86. The valve 81 is shut periodically. The pressure sensor 88 senses the pressure of the sample gas 12 in the volume chamber 86. When the valve 81 is closed, the control system 20 can determine the time rate of change of the pressure in volume 86 from continuous or periodic signals from the pressure sensor 88. The time rate of change of pressure drop in the volume 86 is proportional to the mass flowrate $CO_b$ of sample gas 12 through pore 84. The value obtained for the mass flowrate of sample gas 12 through the pore 84 can be squared and inverted in the control system 20 to produce a signal proportional to the density of the sample gas 12 flowing through the pore 84 (i.e. pore density). The base condition density $\rho_b$ of the sample gas 12 is determined by: closing valve 38, opening valve 28, determining a density of the reference gas 26 in the same manner as the pore density, and comparing the density of the reference gas 26 to the pore density.

Having measured the base condition density $\rho_b$ of the sample gas 12, the present invention can measure the ratio $$\left(\frac{Q_f}{Q_f'}\right)$$

even when the sample gas flowmeter 10 does not respond to density in the same manner as the pipeline gas flowmeter 22. Two such systems where the sample gas flowmeter 10 does not respond to density in the same manner are described below: The first is a system having a sample gas flowmeter 10 comprised of a capillary 60 and a differential pressure cell 62 (see FIG. 6). The second is a system where the sample gas flowmeter 10 is a turbine meter 70 with a signal generator 72 (see FIG. 7).

Figure 6:
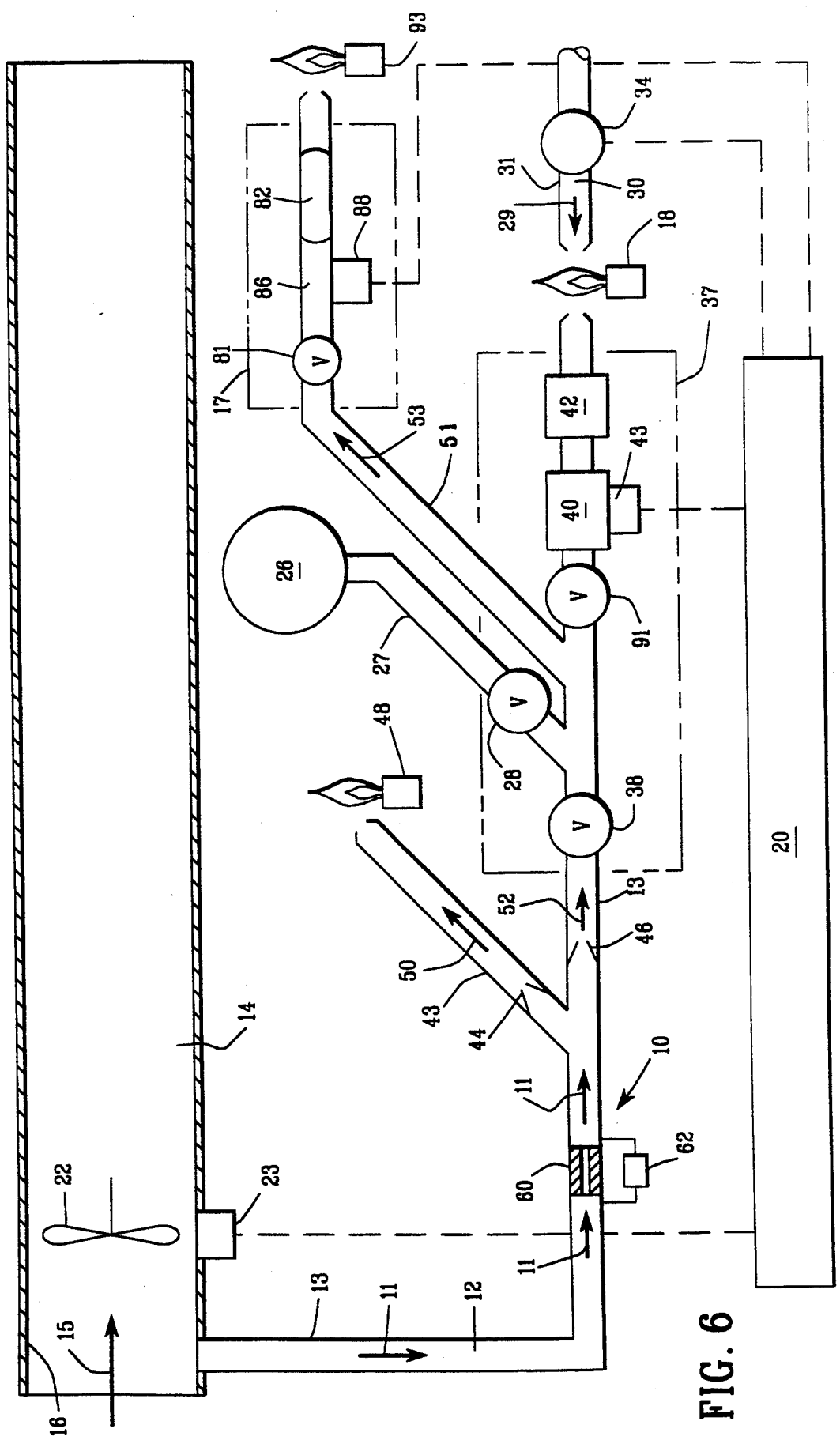
FIG. 6 is a schematic drawing similar to FIG. 1 in which a sample gas flowmeter is a capillary and a differential pressure cell.

Referring to FIG. 6, the differential pressure cell 62 measures the pressure drop $\Delta P_s$ of the sample gas 12 as the sample gas flows through the capillary 60 in the direction of arrows 11. The mass flowrate $\omega_s$ of the sample gas 12 flowing through the capillary 60 can be represented by the following relation:

$$\omega_s = K_s \, C_{Ds} \, Y_s \, d_s^2 \sqrt{\rho_s \, \Delta P_s} \tag{19}$$

where $K_s$ is a scaling constant for the capillary 60, $C_{Ds}$ is a discharge coefficient for the capillary 60, $Y_s$ is an expansion factor of the sample gas 12 flowing through the capillary 60, $d_s$ is a characteristic diameter for the capillary 60, $\rho_s$ is the density of the sample gas 12 flowing through the capillary 60, and $\Delta P_s$ is the pressure drop across the capillary 60. Note that the capillary 60 and the sample gas 12 therein should be maintained at the same temperature as the pipeline gas 14 in the pipeline 16. FIGS. 2 and 3 show suitable arrangements to maintain the temperature in the capillary 60 at substantially the same temperature as the pipeline gas 14 in the pipeline 16.

Capillaries can be made in many forms, and the term "capillary" as used herein refers to a device for obtaining a very small, controlled flowrate. As will be apparent to one skilled in the art, the present invention does not require that the capillary 60 be a conventional capillary tube. Rather, any apparatus that allows the flow of sample gas 12 and produces a pressure differential is sufficient. It is preferred, however, that the capillary 60 be a tortuous path capillary tube as is described in patent application Ser. Nos. 08/009,481, filed Jan. 25, 1993 and 07/787,188, filed Nov. 4, 1991. The disclosure in these patent applications is hereby incorporated by reference. The advantage of the tortuous path capillary tube is that the discharge coefficient $C_{Ds}$ is more stable.

The mass flowrate $\omega_s$ of the sample gas through the capillary 60 can be given by the following description:

$$\omega_s = Q_f' \rho_s \tag{20}$$

where $Q_f'$ is the volumetric flowrate of the sample gas 12 through the capillary 60 and $\rho_s$ is the density of the sample gas 12 flowing through the capillary 60. Unless a flow splitter (i.e. sonic nozzles 44 and 46) is used to split the flow of sample gas 12 before it flows to the burner 18, the mass flowrate $\omega_s$ of the sample gas flowing through the capillary 60 is equal to the mass flowrate $\omega_b$ of the sample gas 12 flowing to the burner 18 (i.e. $\omega_s = \omega_b$). Assuming that all of the sample gas 12 flowing through the capillary 60 also flows through valve 38, the mass flowrate $\omega_b$ of the sample gas 12 through valve 38 is given by the following relation:

$$\omega_b = \rho_b Q_b' = \rho_b (E_{sample\ gas}/H_{sample\ gas}) \tag{21}$$

where $\rho_b$ is measured by the densitometer 17 and $Q_b'$ (i.e. $E_{sample\ gas}/H_{sample\ gas}$) is determined by burning the sample gas 12 with air 30 as discussed above. If a flow splitter is used, $\omega_s = S\omega_b$, and this modification should be reflected in Eq. (21) and the following associated analysis.

Setting Eq. (19) and (21) equal to one another (i.e. $\omega_s = \omega_b$), solving for $\sqrt{\rho_s}$, and squaring the result gives the following relation for the density $\rho_s$ of the sample gas 12 flowing through the capillary 60:

$$\rho_s = \frac{\rho_b^2 \left( \dfrac{E_{sample\ gas}}{H_{sample\ gas}} \right)^2}{K_s^2 \, C_{Ds}^2 \, Y_s^2 \, d_s^2 \, \Delta P_2} \tag{22}$$

Referring again to FIG. 6, the volumetric flowrate $Q_f$ of the pipeline gas 14 flowing through the pipeline 16 is measured by a turbine meter 22 having an associated signal generator 23 which sends a frequency signal $f_t$ to the control system 20. The volumetric flowrate $Q_f$ of the pipeline gas 14 flowing through the pipeline can be represented by:

$$Q_f = K_t f_t \tag{23}$$

where $K_t$ is a scaling constant.

Since the volumetric flowrate $Q_f'$ of the sample gas 12 flowing through the capillary 60 is $\omega_s/\rho_s$, it can be seen from Eqs. (19), (22), and (23) that the ratio $$\left( \frac{Q_f}{Q_f'} \right)$$

is equal to:

$$\frac{Q_f}{Q_f'} = \frac{K_t f_t \rho_b \left( \dfrac{E_{sample\ gas}}{H_{sample\ gas}} \right)^2}{K_s^2 \, C_{Ds}^2 \, Y_s^2 \, d_s^2 \, \Delta P_s} \tag{24}$$

Thus, the ratio $$\left( \frac{Q_f}{Q_f'} \right)$$

can be determined without knowing the density $\rho_s$ of the sample gas 12 flowing through the capillary 60. While the embodiment shown in FIG. 6 shows a turbine flowmeter 22 monitoring the volumetric flowrate $Q_f$ of the pipeline gas 14 flowing through the pipeline 16, it should be noted that the volumetric flowrate $Q_f$ can be measured by other means, although Eqs. (23) and (24) would have to be altered correspondingly.

Referring to FIG. 7, the sample gas flowmeter 10 in this embodiment is a turbine flowmeter 70 located in line 13. As the sample gas 12 flows through the turbine sample gas flowmeter 70 in the direction of arrows 11, a signal generator 72 generates a signal $f_s$ representing the frequency that the turbine 70 rotates. The frequency signal $f_s$ is electrically transmitted to the control system 20. The volumetric flowrate $Q_f'$ of the sample gas 20 flowing through the sample gas turbine meter 70 can be represented by:

$$Q_f' = K_s f_s \tag{25}$$

where $K_s$ is a scaling constant for the sample gas turbine meter 70, and $f_s$ is a frequency signal from the sample gas turbine meter 70.

In FIG. 7, the volumetric flow $Q_f$ of the pipeline gas 14 flowing through the pipeline 16 is measured using an orifice 74 and a differential pressure cell 76. The differential pressure cell 76 monitors the pressure drop $\Delta P_f$ of the pipeline gas 14 as it flows through the orifice 74 in the direction of arrow 15. It measures the differential pressure drop $\Delta P_f$ across orifice 74 by monitoring the pipeline gas 14 pressure at point 78 before the orifice 74 and at point 80 after the orifice 74.

The differential pressure cell 76 sends a signal representing the pressure difference $\Delta P_f$ to the control system 20. The volumetric flow $Q_f$ through the orifice 74 can be represented by the following expression:

$$Q_f = K_f C_{Df} Y_f d_f^2 \frac{\sqrt{\Delta P_f}}{\sqrt{\rho_f}} \quad (26)$$

where $K_f$ is a scaling constant for the orifice 74, $C_{Df}$ is a discharge coefficient for the orifice 74, $Y_f$ is an expansion coefficient for the pipeline gas flowing through the orifice 74, $d_f$ is a characteristic diameter for the orifice 74, $\rho_f$ is the density of the pipeline gas 14 flowing through the orifice 74, and $\Delta P_f$ is the differential pressure as measured by the differential pressure cell 76. Since the sample gas 12 flowing through the turbine meter 70 is maintained at the same temperature and pressure as the pipeline gas (see FIGS. 2 and 3), the density $\rho_f$ of the pipeline gas 14 flowing through the orifice 74 is equal to the density $\rho_s$ of the sample gas 12 flowing through the sample gas flowmeter 70. Therefore, Eq. (26) can be rewritten as:

$$Q_f = K_f C_{Df} Y_f d_f^2 \frac{\sqrt{\Delta P_f}}{\sqrt{\rho_s}} \quad (27)$$

Assuming that all of the sample gas 12 flowing through the turbine meter 70 flows through valve 38 (i.e. no flow splitting by sonic nozzles 44 and 46), the mass flowrate $\omega_s$ of the sample gas flowing through the turbine 70 is equal to the mass flowrate $\omega_b$ of the sample gas 12 flowing through valve 38. This can be represented by:

$$Q_f' \rho_s = Q_b' \rho_b \quad (28a)$$

or $$Q_f' \rho_s = S Q_b' \rho_b \quad (28b)$$

if flow splitting occurs. Therefore, the density $\rho_s$ of the sample gas 12 flowing through the sample gas turbine meters 70 can be represented by:

$$\rho_s = \rho_b \frac{Q_b'}{Q_f'} = \rho_b \frac{E_{sample\ gas}}{H_{sample\ gas} K_s f_s} \quad (29)$$

Equation (29) can be substituted into Eq. (27), and the ratio $$\left( \frac{Q_f}{Q_f'} \right)$$

becomes:

$$\frac{Q_f}{Q_f'} = \frac{K_f C_{Df} Y_f d_f^2 \sqrt{\Delta P_f}}{\sqrt{\rho_b \frac{E_{sample\ gas} K_s f_s}{H_{sample\ gas}}}} \quad (30)$$

In Eq. (30), $K_f$, $C_{Df}$, $Y_f$, $d_f$, and $K_s$ are constants. The other variables ($\Delta P_f$, $\rho_b$, $E_{sample\ gas}$, $F_{sample\ gas}$, and $f_s$) are measured as discussed above, and signals representing their magnitude are electronically sent to the control system 20. If there is flow splitting by sonic nozzles 44 and 46, Eq. (30) should be modified by multiplying $\rho_b$ in the denominator of Eq. (30) by the split ratio S.

Many modifications and variations of these preferred embodiments that are within the scope and spirit of the invention will be apparent to those with ordinary skill in the art.

I claim:

1. A method for measuring a base condition volumetric flowrate ($Q_b$) of a pipeline gas flowing through a pipeline which corresponds to a volumetric flowrate at a base condition pressure and temperature, the method comprising:

measuring a flowrate ($Q_f$) of the pipeline gas flowing through the pipeline with a linear pipeline gas flowmeter;

determining a volumetric correction ratio by:

flowing sample gas from the pipeline to a capillary, measuring a pressure drop of the sample gas across the capillary as the sample gas flows through the capillary, maintaining the temperature of the sample gas as the sample gas flows through the capillary at substantially the same temperature as the pipeline gas in the pipeline, measuring an energy flowrate (energy per unit time) of the sample gas ($E_{sample\ gas}$) which is equivalent to an energy flowrate of the sample gas at a base condition temperature and pressure, measuring a heating value (energy per unit volume) of the sample gas ($H_{sample\ gas}$) which is equivalent to a heating value of the sample gas at the base condition temperature and pressure, measuring a base condition density of the sample gas which is equivalent to a density of the sample gas at the base condition temperature and pressure, and calculating the volumetric correction ratio from the pressure drop, the energy flowrate, the heating value, and the density; and adjusting the flowrate ($Q_f$) of the pipeline gas as measured by the linear pipeline gas flowmeter by the volumetric correction ratio.

2. A method as recited in claim 1 wherein the sample gas heating value ($H_{sample\ gas}$) is measured by:

flowing the sample gas to a burner at a sample gas volumetric flowrate ($Q_{sample\ gas}$) and burning the sample gas with air flowing to the burner at a sample gas air flowrate ($\omega_{air\ sample}$), the sample gas air flowrate ($\omega_{air\ sample}$) being of such relative magnitude to the sample gas volumetric flowrate ($Q_{sample}$

*gas*) so that the sample gas burns at maximum flame temperature;

intermittently flowing a reference gas to the burner at a reference gas volumetric flowrate ($Q_{reference\ gas}$) and burning the reference gas with air flowed to the burner at a reference gas air flowrate ($\omega_{air\ reference}$), the reference gas air flowrate ($\omega_{air\ reference}$) being of such relative magnitude to the reference gas volumetric flowrate ($Q_{reference\ gas}$) so that the reference gas burns at maximum flame temperature; and calculating the sample gas heating value ($H_{sample\ gas}$) by the following expression:

$$H_{sample\ gas} = H_{reference\ gas} \frac{(Q_{sample\ gas})}{(Q_{reference\ gas})} \frac{(\omega_{air\ sample})}{(\omega_{air\ reference})}$$

where $H_{reference\ gas}$ is a known heating value for the reference gas.

3. A method as recited in claim 2 wherein the ratio $$\left( \frac{Q_{sample\ gas}}{Q_{reference\ gas}} \right)$$

of the sample gas volumetric flowrate ($Q_{sample\ gas}$) to the burner compared to the reference gas volumetric flowrate ($Q_{reference\ gas}$) to the burner is determined by:

filling a chamber with sample gas;
flowing the sample gas from the chamber;
measuring a time rate of change of sample gas pressure $$\left( \left( \frac{dP}{dt} \right)_{sample\ gas} \right)$$

as the sample gas flows from the chamber at a measuring pressure;

filling the chamber with reference gas;
flowing the reference gas from the chamber;
measuring a time rate of change of reference gas pressure $$\left( \left( \frac{dP}{dt} \right)_{reference\ gas} \right)$$

as the reference gas flows from the chamber at substantially the measuring pressure used for measuring the time rate of change of the sample gas pressure; and dividing the time rate of change of the sample gas pressure $$\left( \left( \frac{dP}{dt} \right)_{sample\ gas} \right)$$

by the time rate of change of the reference gas pressure $$\left( \left( \frac{dP}{dt} \right)_{reference\ gas} \right)$$

to determine the ratio $$\left( \frac{Q_{sample\ gas}}{Q_{reference\ gas}} \right).$$

4. A method as recited in claim 1 wherein the sample gas energy flowrate ($E_{sample\ gas}$) is measured by:

flowing sample gas from the capillary to a burner;
burning the sample gas in the burner with air flowing to the burner at an air flowrate ($\omega_{air}$);
adjusting the air flowrate ($\omega_{air}$) to the burner so that the sample gas burns at maximum flame temperature;
determining the adjusted air flowrate ($\omega_{air}$); and
calculating the sample gas energy flowrate ($E_{sample\ gas}$) by the following relation:

$$E_{sample\ gas} = K_{max-air} \omega_{air}$$

where $K_{max-air}$ is a constant.

5. A method as recited in claim 1 wherein the sample gas energy flowrate ($E_{sample\ gas}$) is measured by:

flowing sample gas from the capillary to a burner;
burning the sample gas in the burner with air flowing to the burner at a constant air flowrate;
adjusting the flowrate of the sample gas to the burner so that the sample gas burns at maximum flame temperature;
determining the sample gas energy flowrate ($E_{sample\ gas}$) using the following relation:

$$E_{sample\ gas} = K_{max-air} \omega_{air}$$

where $K_{max-air}$ is a constant, and $\omega_{air}$ is the air flowrate.

6. A method as recited in claim 1 wherein the base condition density of the sample gas is measured by:

flowing sample gas from the capillary into a chamber;
stopping the flow of sample gas into the chamber;
flowing sample gas from the chamber through a pore, the pore being sized so that the square of the sample gas mass flowrate through the pore is inversely proportional to the density of the sample gas flowing through the pore;
measuring the time rate of change of the pressure in the chamber as sample gas flows through the pore;
deriving a density of the sample gas as proportional to the inverse of the square of the time rate of change of pressure in the chamber; and
comparing the density of the sample gas to the density of a reference gas measured in a like manner.

7. A method for measuring a base condition volumetric flowrate ($Q_b$) of a pipeline gas flowing through a pipeline which corresponds to a volumetric flowrate at a defined pressure and temperature:

measuring a flowrate ($Q_f$) of the pipeline gas flowing through the pipeline with a differential pressure pipeline gas flowmeter;
determining a volumetric correction ratio by:
flowing sample gas from the pipeline to a linear sample gas flowmeter,
measuring a sample gas flowrate with the linear sample gas flowmeter,
maintaining the temperature of the sample gas at substantially the same temperature as the pipeline gas in the pipeline when the sample gas flowrate is measured by the linear sample gas flowmeter, measuring an energy flowrate (energy per unit time) of the sample gas ($E_{sample\ gas}$) which is equivalent to an energy flowrate of the sample gas at a base condition temperature and pressure, measuring a heating value (energy per unit volume) of the sample gas ($H_{sample\ gas}$) which is equivalent to a heating value of the sample gas at a base condition temperature and pressure, measuring a base condition density of the sample gas which is equivalent to a density of the sample gas at a base condition temperature and pressure, and calculating the volumetric correction ratio from the sample gas flowrate, the energy flowrate, the heating value, and the density; and adjusting the flowrate ($Q_f$) of the pipeline gas flowing through the pipeline in relation to the volumetric correction ratio.

8. A method as recited in claim 7 further comprising the step of: splitting the flow of sample gas flowing from the linear sample gas flowmeter into a waste stream and a test stream after the sample gas flows through the linear sample gas flowmeter, wherein the sample gas energy flowrate ($E_{sample\ gas}$) is measured by measuring the energy flowrate of the test stream and multiplying the energy flowrate of the test stream by a ratio of a mass flowrate of the sample gas flowing from the linear sample gas flowmeter compared to a mass flowrate of the test stream.

9. A method as recited in claim 8 further comprising the step of burning the waste stream of the sample gas in a catalytic burner.

10. A method as recited in claim 7 wherein the sample gas heating value ($H_{sample\ gas}$) is measured by:

flowing the sample gas to a burner at a sample gas volumetric flowrate ($Q_{sample\ gas}$) and burning the sample gas with air flowing to the burner at a sample gas air flowrate ($\omega_{air\ sample}$), the sample gas air flowrate ($\omega_{air\ sample}$) being of such relative magnitude to the sample gas volumetric flowrate ($Q_{sample\ gas}$) so that the sample gas burns at maximum flame temperature;

intermittently flowing a reference gas to the burner at a reference gas volumetric flowrate ($Q_{reference\ gas}$) and burning the reference gas with air flowed to the burner at a reference gas air flowrate ($\omega_{air\ reference}$), the reference gas air flowrate ($\omega_{air\ reference}$) being of such relative magnitude to the reference gas volumetric flowrate ($Q_{reference\ gas}$) so that the reference gas burns at maximum flame temperature; and calculating the sample gas heating value ($H_{sample\ gas}$) by the following expression:

$$H_{sample\ gas} = H_{reference\ gas} \frac{Q_{sample\ gas}}{Q_{reference\ gas}} \frac{\omega_{air\ sample}}{\omega_{air\ reference}}$$

where $H_{reference\ gas}$ is a known heating value for the reference gas.

11. A method as recited in claim 10 wherein the ratio $$\left( \frac{Q_{sample\ gas}}{Q_{reference\ gas}} \right)$$

of the sample gas volumetric flowrate ($Q_{sample\ gas}$) to the burner compared to the reference gas volumetric flowrate ($Q_{reference\ gas}$) to the burner is determined by:

filling a chamber with sample gas;
flowing the sample gas from the chamber;
measuring a time rate of change of sample gas pressure $$\left( \left( \frac{dP}{dt} \right)_{sample\ gas} \right)$$

as the sample gas flows from the chamber at a measuring pressure;

filling the chamber with reference gas;
flowing the reference gas from the chamber;
measuring a time rate of change of reference gas pressure $$\left( \left( \frac{dP}{dt} \right)_{reference\ gas} \right)$$

as a reference gas flows from the chamber at substantially the same measuring pressure as the sample gas; and dividing the time rate of change of the sample gas pressure $$\left( \left( \frac{dP}{dt} \right)_{sample\ gas} \right)$$

by the time rate of change of the reference gas pressure $$\left( \left( \frac{dP}{dt} \right)_{reference\ gas} \right)$$

to determine the ratio $$\left( \frac{Q_{sample\ gas}}{Q_{reference\ gas}} \right).$$

12. A method as recited in claim 7 wherein the sample gas energy flowrate ($E_{sample\ gas}$) is measured by:

flowing sample gas from the linear sample gas flowmeter;
burning the sample gas in the burner with air flowing to the burner at a constant air flowrate;
adjusting the flowrate of the sample gas to the burner so that the sample gas burrus at maximum flame temperature;
determining the sample gas energy flowrate ($E_{sample\ gas}$) using the following relation:

$$E_{sample\ gas} = K_{max-air} \omega_{air}$$

where $K_{max-air}$ is a constant, and $\omega_{air}$ is the air flowrate.

13. A method as recited in claim 7 wherein the sample gas energy flowrate ($E_{sample\ gas}$) is measured by:

flowing sample gas from the linear sample gas flowmeter to a burner;
burning the sample gas in the burner with air flowing to the burner at an air flowrate ($\omega_{air}$);

adjusting the air flowrate (O3air) to the burner so that the sample gas burns at maximum flame temperature;

determining the adjusted air flowrate ($\omega_{air}$); and determining the sample gas energy flowrate ($E_{sample\,gas}$) using the following relation:

$$E_{sample\,gas} = K_{max-air} \omega_{air}$$

where $K_{max-air}$ is a constant.

14. A method as recited in claim 7 wherein the base condition density of the sample gas is measured by:

flowing sample gas from the linear sample gas flowmeter into a chamber;

stopping the flow of sample gas into the chamber;

flowing sample gas from the chamber through a pore, the pore being sized so that the square of the sample gas mass flowrate through the pore is inversely proportional to the density of the sample gas flowing through the pore;

measuring the time rate of change of the pressure in the chamber as the sample gas flows through the pore;

deriving a density of the sample gas as proportional to the inverse of the square of the time rate of change of pressure in the chamber; and comparing the density of the sample gas to the density of a reference gas measured in a like manner.

15. A volumetric flow corrector comprising:

a conduit for flowing sample gas from a pipeline;

a sample gas flowmeter for measuring a flowrate ($Q_f$) of the sample gas through the conduit, the sample gas being maintained at substantially the same temperature as the pipeline gas in the pipeline when the sample gas flowmeter measures the flowrate ($Q_f$) of the sample gas;

a sample gas energy flowmeter for measuring an energy flowrate ($E_{sample\,gas}$) (energy per unit time) of the sample gas flowing through the conduit which is equivalent to an energy flowrate of the sample gas flowing through the conduit at a base condition temperature and pressure;

a sample gas heating value meter for measuring a heating value ($H_{sample\,gas}$) (energy per unit volume) of the sample gas flowing through the conduit which is equivalent to a heating value of the sample gas flowing through the conduit at a base condition temperature and pressure; and a densitometer for measuring a base condition density of the sample gas flowing through the conduit which is equivalent to a density of the sample gas flowing through the conduit at a base condition temperature and pressure;

and further comprising a control system which receives a signal representing the flowrate ($Q_f$) of the sample gas from the sample gas flowmeter, a signal representing the energy flowrate ($E_{sample\,gas}$) of the sample gas from the sample gas energy flowmeter, a signal representing the heating value ($H_{sample\,gas}$) of the sample gas from the sample gas heating value meter, and a signal representing the base condition density of the sample gas, and calculates a volumetric correction ratio from the sample gas flowrate ($Q_f$), the energy flowrate ($E_{sample\,gas}$) of the sample gas, the heating value ($H_{sample\,gas}$) of the sample gas, and the base condition density ($\rho_{sample\,gas}$) of the sample gas.

16. A volumetric flow corrector as recited in claim 15 further comprising:

a mass flow splitter for splitting the flow of sample gas flowing through the conduit into a test stream and a waste stream after the sample gas flowmeter measures the sample gas flowrate ($Q_f$) through the conduit, wherein the sample gas energy flowmeter measures the energy flowrate of the sample gas by measuring the energy flowrate of the test stream and multiplying the energy flowrate of the test stream by a ratio of a mass flowrate of the sample gas flowing from the sample gas flowmeter compared to the mass flowrate of the test stream.

17. A volumetric flow corrector as recited in claim 16 further comprising a catalytic burner for burning the sample gas in the waste stream.

18. A volumetric flow corrector as recited in claim 15 wherein the energy flowmeter comprises:

a burner for burning sample gas flowing through the conduit from the sample gas flowmeter with air flowing at an air flowrate ($\omega_{air}$) to form a flame burning at a flame temperature;

a temperature sensor for measuring the flame temperature; and an air flow adjustor for adjusting the air flowrate ($\omega_{air}$) so that the sample gas burns at a maximum flame temperature.

19. A volumetric flow corrector as recited in claim 15 wherein the energy flowmeter comprises:

a burner for burning sample gas flowing through the conduit from the sample gas flowmeter with air flowing at an air flowrate ($\omega_{air}$) to form a flame burning at a flame temperature;

a temperature sensor for measuring the flame temperature; and a sample gas flow adjustor for adjusting the sample gas flowrate to a burner so that the sample gas burns at a maximum flame temperature.

20. A volumetric flow corrector as recited in claim 15 wherein the sample gas heating value meter comprises:

a burner for burning sample gas flowing at a sample gas flowrate ($Q_{sample\,gas}$) with air flowing at a sample gas air flowrate ($\omega_{air\,sample}$), the sample gas air flowrate ($\omega_{air\,sample}$) being of such relative magnitude to the sample gas flowrate ($Q_{sample\,gas}$) so that the sample gas burns at maximum flame temperature; and a reference gas that is intermittently flowed to the burner at a reference gas flowrate ($Q_{reference\,gas}$) and burned with air flowing to the burner at a reference gas air flowrate ($\omega_{reference\,gas}$), the reference gas air flowrate ($\omega_{air\,reference}$) being of such relative magnitude to the reference gas flowrate ($Q_{reference\,gas}$) so that the reference gas burns at maximum flame temperature;

wherein the heating value of the sample gas ($H_{sample\,gas}$) is determined in the control system by the following expression:

$$H_{sample\,gas} = H_{reference\,gas} \frac{(Q_{reference\,gas})(\omega_{air\,sample})}{(Q_{sample\,gas})(\omega_{air\,reference})}$$

where $H_{reference\,gas}$ is a known heating value for the reference gas at base condition temperature and pressure.

21. A volumetric flow corrector as claimed in claim 15 wherein the densitometer comprises:

a chamber connected to receive sample gas flowing through the conduit;

a valve for controlling the flow of gas to the chamber;

a flow restrictor for restricting the flow of gas from the chamber;

a pressure sensor for measuring the pressure in the chamber; and means for determining a time rate of change of pressure in the chamber as the gas flows through the flow restrictor.

22. A volumetric flow corrector as recited in claim 15 wherein the sample gas flowmeter is a linear flowmeter.

23. A volumetric flow corrector as recited in claim 15 wherein the sample gas flowmeter is a differential pressure flowmeter.

24. A volumetric flow corrector as recited in claim 23 wherein the sample gas differential pressure flowmeter comprises:

a capillary; and a differential pressure cell for measuring the pressure drop of sample gas flowing through the capillary.

* * * * *